United States Patent
Balaji et al.

(10) Patent No.: US 11,625,999 B2
(45) Date of Patent: Apr. 11, 2023

(54) NON-OBTRUSIVE METHOD AND SYSTEM FOR DETECTION OF EMOTIONAL LONELINESS OF A PERSON

(71) Applicant: Tata Consultancy Services Limited, Mumbai (IN)

(72) Inventors: Ramesh Balaji, Chennai (IN); Anirudh Thenguvila Purushothaman, Kochi (IN); Srinivasa Raghavan Venkatachari, Chennai (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 0 days.

(21) Appl. No.: 17/453,335

(22) Filed: Nov. 2, 2021

(65) Prior Publication Data
US 2023/0026032 A1 Jan. 26, 2023

(30) Foreign Application Priority Data
Jun. 30, 2021 (IN) .............................. 202121029498

(51) Int. Cl.
*G08B 21/04* (2006.01)
*A61B 5/16* (2006.01)

(52) U.S. Cl.
CPC .......... *G08B 21/0423* (2013.01); *A61B 5/165* (2013.01); *G08B 21/0415* (2013.01); *G08B 21/0469* (2013.01); *G08B 21/0492* (2013.01)

(58) Field of Classification Search
CPC ............ G08B 21/0423; G08B 21/0415; G08B 21/0469; G08B 21/0492; A61B 5/165
See application file for complete search history.

(56) References Cited

U.S. PATENT DOCUMENTS 8,903,176 B2 * 12/2014 Hill ..................... G10L 15/1815
715/753
11,120,226 B1 * 9/2021 Nudd ..................... G16H 50/30
(Continued)

FOREIGN PATENT DOCUMENTS

WO WO2015124972 A1 8/2015

OTHER PUBLICATIONS

Dickerson, Robert F. et al., "Empath: a Continuous Remote Emotional Health Monitoring System for Depressive Illness", Conference: Proceedings of Wireless Health, Date: Oct. 2011, pp. 1-10, Publisher: ACM, https://www.cs.virginia.edu/~stankovic/psfiles/robempath.pdf.

(Continued)

*Primary Examiner* — Curtis J King
(74) *Attorney, Agent, or Firm* — Finnegan, Henderson, Farabow, Garrett & Dunner LLP (57) ABSTRACT

Emotional loneliness is referred as the absence of an attachment figure in one's life and someone to turn to. The existing methods use installation of sensors for tracking the movement, behaviour and activity of the person, but most of the efforts are obtrusive in nature. A non-obtrusive method and system for detection of emotional loneliness of a person have been provided. The disclosure is utilizing multiple varied techniques to understand the emotional loneliness. The multiple techniques comprise room change movement anomalies, living room stay anomalies, correlating the living room stay with the bedroom stay and outdoor movement anomalies. The methodology also ensures reduced variance and false positives, as emotional loneliness is finally determined based on more than two positives of above methods. The detection of person's movement is done using a featured engineered dataset based on collection of raw time series data collected from a plurality of motion sensors.

15 Claims, 7 Drawing Sheets

(56) References Cited

U.S. PATENT DOCUMENTS

| | | | |
|---|---|---|---|
| 11,260,536 B1* | 3/2022 | Kim | B25J 11/001 |
| 11,436,549 B1* | 9/2022 | Hull | G06Q 10/06398 |
| 2002/0091307 A1* | 7/2002 | Kanter | A61B 5/16 |
| | | | 600/300 |
| 2005/0068183 A1* | 3/2005 | Yuasa | A01K 29/00 |
| | | | 340/573.1 |
| 2005/0137465 A1 | 6/2005 | Cuddihy et al. | |
| 2009/0256710 A1* | 10/2009 | Duckert | G08B 21/0484 |
| | | | 340/573.1 |
| 2010/0107075 A1* | 4/2010 | Hawthorne | G06Q 10/06 |
| | | | 715/708 |
| 2011/0179159 A1* | 7/2011 | Eglington | G08B 21/0423 |
| | | | 709/224 |
| 2012/0053472 A1 | 3/2012 | Tran | |
| 2012/0143693 A1* | 6/2012 | Chung | G06Q 30/0241 |
| | | | 709/224 |
| 2014/0095150 A1* | 4/2014 | Berjikly | G06F 40/40 |
| | | | 704/9 |
| 2014/0101296 A1* | 4/2014 | Li | H04L 41/0813 |
| | | | 709/221 |
| 2016/0196735 A1* | 7/2016 | Clayman | G08B 25/016 |
| | | | 340/573.1 |
| 2021/0011975 A1* | 1/2021 | Aarabi | G06F 40/30 |
| 2022/0028426 A1* | 1/2022 | Park | G11B 27/031 |

OTHER PUBLICATIONS

Toh, Xiao Ping et al., "Sensor-Driven Detection of Social Isolation in Community-Dwelling Elderly", Human Aspects of IT for the Aged Population. Applications, Services and Contexts, Date: May 2017, pp. 378-392, Publisher: Springer, https://ink.library.smu.edu.sg/cgi/viewcontent.cgi?article?4733&context=sis_research.

Austin, Johanna et al., "A Smart-Home System to Unobtrusively and Continuously Assess Loneliness in Older Adults", IEEE Journal of Translational Engineering in Health and Medicine, Date: Jun. 2016, Publisher: IEEE, https://www.researchgate.net/publication/303905864_A_Smart-Home_System_to_Unobtrusively_and_Continuously_Assess_Loneliness_in_Older_Adults/link/578d023408ae7a588ef3d89d/download.

* cited by examiner

NON-OBTRUSIVE METHOD AND SYSTEM FOR DETECTION OF EMOTIONAL LONELINESS OF A PERSON

PRIORITY CLAIM

This U.S. patent application claims priority under 35 U.S.C. § 119 to: India Application No. 202121029498, filed on 30 Jun. 2021. The entire contents of the aforementioned application are incorporated herein by reference.

TECHNICAL FIELD

The disclosure herein generally relates to the field of emotional loneliness detection, and, more particularly, to a non-obtrusive method and system for detection of emotional loneliness of a person, especially an elderly person.

BACKGROUND

Loneliness has been defined as 'a discrepancy between one's desired and achieved levels of social relations'. The emotional loneliness is referred as the absence of an attachment figure in one's life and absence of someone to turn to for support. Elderly living alone often has a limited network of family and friends, with high risk of social deprivation, leading to pertinent issues such as emotional loneliness/isolation. With a considerably large ageing population across the world, the risks faced by the elderly people living alone could range from their safety and health to their psychological well-being related aspects.

Research studies through survey and interviews undertaken on elderly find that emotional loneliness in a home environment means an elderly person spends a lot of time in a living room and his napping time on bedroom during day time decreases a lot. This suggests that the elderly who lack an attachment figure or who do not have anyone to turn to when they need emotional comfort, would spend more time in the living room.

Various efforts have been made in the past for improving the emotional condition of elderly people. Few methods use installation of sensors for tracking the movement of the person, but most of the efforts are obtrusive in nature and disturb the privacy of the person. In addition to that these efforts are not accurate enough to come out to any conclusion.

SUMMARY

Embodiments of the present disclosure present technological improvements as solutions to one or more of the above-mentioned technical problems recognized by the inventors in conventional systems. For example, in one embodiment, a system for detection of emotional loneliness of a person is provided. The system comprises a plurality of motion sensors, one or more hardware processors and a memory. The plurality of motion sensors collects a first set of input data, the plurality of motion sensors configured to sense movement of the person at predefined time intervals over a time period, wherein the plurality of motion sensors is present in a plurality of rooms at a facility, wherein the plurality of rooms comprises one or more living rooms, one or more bedrooms, and one or more bathrooms. The memory is in communication with the one or more hardware processors, wherein the one or more hardware processors are configured to execute programmed instructions stored in the memory, to: perform a set of feature engineering techniques on the first set of input data to get a featured sensor dataset; create a local outlier factor (LOF) model using the featured sensor dataset with time spent by the person in the living room during day time as an attribute, wherein the day time is time between 7.00 AM and 7.00 PM; extract a set of instances using the LOF model; indicate a first emotional isolation indicator as "YES", if 40% of extracted set of instances have a time spent in the living room is more than a first threshold; find a correlation between a time spent in the bedroom and a time spent in the living room using a Pearson correlation, wherein the time spent in the bedroom and living room is derived from featured sensor dataset; find a number of samples in which the time spent in the living room stay is more than the time spent in the bedroom; indicate a second emotional isolation indicator as "YES", if the correlation is negative and in more than 40% of samples the time spent in living room is more than time spent in the bedroom; detect the time spent by the person outside the facility for every day during the daytime; indicate a third emotional isolation indicator as "YES", if more than 40% of the detected time spent by the person out of the home is less than a second predefined threshold; detect a number of room changes made by the person during the day time; indicate a fourth emotional isolation indicator as "YES", if more than 40% of the detected number of room changes is less than a third predefined threshold time; and identify the person being as emotionally lone, if out of the first emotional isolation indicator, the second emotional isolation indicator, the third emotional isolation indicator, and the fourth emotional isolation indicator, more than two emotional isolation indicators indicates "YES".

In another aspect, a method for detection of emotional loneliness of a person is provided. Initially, a first set of input data is collected using a plurality of motion sensors configured to sense movement of the person at predefined time intervals over a time period, wherein the plurality of motion sensors is present in a plurality of rooms at a facility, wherein the plurality of rooms comprises one or more living rooms, one or more bedrooms, and one or more bathrooms. A set of feature engineering techniques is then performed on the first set of input data to get a featured sensor dataset. In the next step, a local outlier factor (LOF) model is created using the featured sensor dataset with time spent by the person in the living room during day time as an attribute, wherein the day time is time between 7.00 AM and 7.00 PM. A set of instances is extracted using the LOF model. Further, a first emotional isolation indicator is indicated as "YES", if 40% of extracted set of instances have a time spent in the living room is more than a first threshold. In the next step, a correlation is found between a time spent in the bedroom and a time spent in the living room using a Pearson correlation, wherein the time spent in the bedroom and living room is derived from featured sensor dataset. A number of samples is then found in which the time spent in the living room stay is more than the time spent in the bedroom. Further, a second emotional isolation indicator is indicated as "YES", if the correlation is negative and in more than 40% of samples the time spent in living room is more than time spent in the bedroom. In the next step, the time spent by the person outside the facility is detected for every day during the daytime. Further, a third emotional isolation indicator is indicated as "YES", if more than 40% of the detected time spent by the person out of the home is less than a second predefined threshold. In the next step, a number of room changes made by the person during the day time is detected. Further, a fourth emotional isolation indicator is indicated as "YES", if more than 40% of the detected number of room changes is less than a third threshold time. And finally, the person is being identified as emotionally lone, if out of the first emotional isolation indicator, the second emotional isolation indicator, the third emotional isolation indicator, and the fourth emotional isolation indicator, more than two emotional isolation indicators indicates "YES".

In yet another aspect, one or more non-transitory machine-readable information storage mediums comprising one or more instructions which when executed by one or more hardware processors cause detection of emotional loneliness of a person is provided. Initially, a first set of input data is collected using a plurality of motion sensors configured to sense movement of the person at predefined time intervals over a time period, wherein the plurality of motion sensors is present in a plurality of rooms at a facility, wherein the plurality of rooms comprises one or more living rooms, one or more bedrooms, and one or more bathrooms. A set of feature engineering techniques is then performed on the first set of input data to get a featured sensor dataset. In the next step, a local outlier factor (LOF) model is created using the featured sensor dataset with time spent by the person in the living room during day time as an attribute, wherein the day time is time between 7.00 AM and 7.00 PM. A set of instances is extracted using the LOF model. Further, a first emotional isolation indicator is indicated as "YES", if 40% of extracted set of instances have a time spent in the living room is more than a first threshold. In the next step, a correlation is found between a time spent in the bedroom and a time spent in the living room using a Pearson correlation, wherein the time spent in the bedroom and living room is derived from featured sensor dataset. A number of samples is then found in which the time spent in the living room stay is more than the time spent in the bedroom. Further, a second emotional isolation indicator is indicated as "YES", if the correlation is negative and in more than 40% of samples the time spent in living room is more than time spent in the bedroom. In the next step, the time spent by the person outside the facility is detected for every day during the daytime. Further, a third emotional isolation indicator is indicated as "YES", if more than 40% of the detected time spent by the person out of the home is less than a second predefined threshold. In the next step, a number of room changes made by the person during the day time is detected. Further, a fourth emotional isolation indicator is indicated as "YES", if more than 40% of the detected number of room changes is less than a third threshold time. And finally, the person is being identified as emotionally lone, if out of the first emotional isolation indicator, the second emotional isolation indicator, the third emotional isolation indicator, and the fourth emotional isolation indicator, more than two emotional isolation indicators indicates "YES".

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Emotional loneliness is referred as the absence of an attachment figure in one's life and someone to turn to. The emotional loneliness is very common in elderly people. The existing methods use installation of sensors for tracking the movement, behaviour and activity of the person, but most of the efforts are obtrusive in nature and disturb the privacy of the person. In addition to that these efforts are able to detect isolation, but are not very conclusive to detect the emotional isolation.

The present disclosure provides a non-obtrusive method and system for detection of emotional loneliness of a person. The disclosure provides an unobtrusive privacy preserving method and system of detecting and validating emotional loneliness of the person. The disclosure is utilizing multiple varied techniques to understand the emotional loneliness. The multiple techniques involved in the present approach are room change movement anomalies, living room stay anomalies, correlating the living room stay with the bedroom stay and outdoor movement anomalies. The methodology used in the disclosure ensures reduced variance and false positives, as emotional loneliness is finally determined based on more than two positive of above methods. The detection of person's movement is done using a featured engineered dataset based on collection of raw time series data collected from a plurality of motion sensors. The data is collected from an observation time, further categorized into day based and night time based variables and the plurality of motion sensor locations (bedroom, living room, kitchen, bathroom etc.).

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method.

Figure 1:
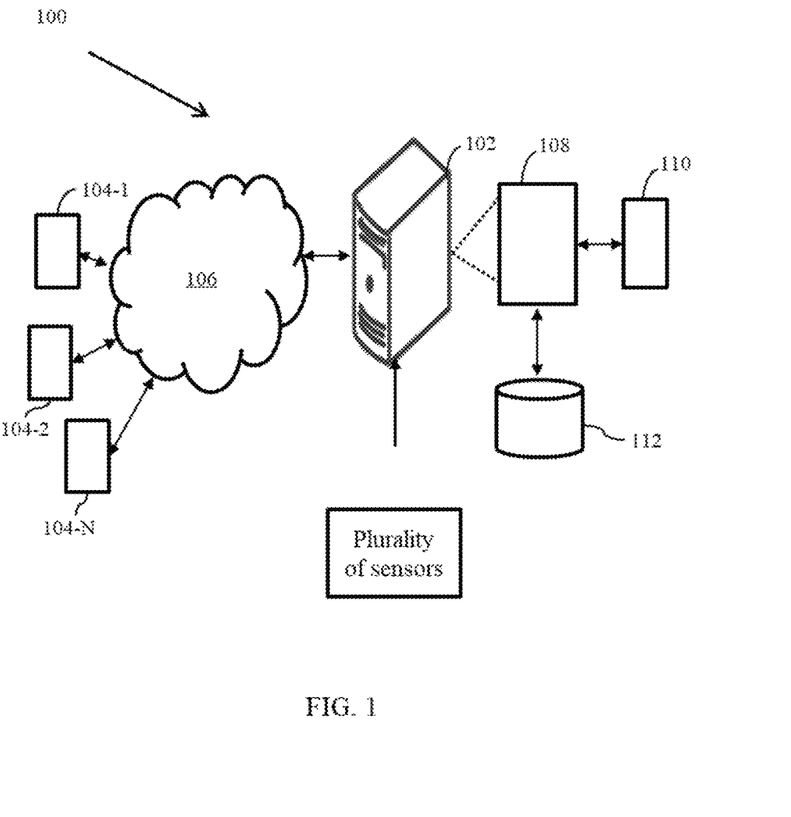
FIG. 1 illustrates a network diagram of a non-obtrusive system for detection of emotional loneliness of a person according to some embodiments of the present disclosure.

According to an embodiment of the disclosure, FIG. 1 illustrates a network diagram of a system 100 for detection of emotional loneliness of a person or a resident. The method is specifically designed for elderly person staying in a home or elderly home or any other facility. The system 100 is a non-obtrusive system and preserves the privacy of the person.

It may be understood that the system 100 comprises one or more computing devices 102, such as a laptop computer, a desktop computer, a notebook, a workstation, a cloud-based computing environment and the like. It will be understood that the system 100 may be accessed through one or more input/output interfaces 104, collectively referred to as I/O interface 104 or user interface 104. Examples of the I/O interface 104 may include, but are not limited to, a user interface, a portable computer, a personal digital assistant, a handheld device, a smartphone, a tablet computer, a workstation and the like. The I/O interface 104 are communicatively coupled to the system 100 through a network 106.

In an embodiment, the network 106 may be a wireless or a wired network, or a combination thereof. In an example, the network 106 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 106 may include a variety of network devices, including routers, bridges, servers, computing devices, storage devices. The network devices within the network 106 may interact with the system 100 through communication links.

The system 100 may be implemented in a workstation, a mainframe computer, a server, and a network server. In an embodiment, the computing device 102 further comprises one or more hardware processors 108, one or more memory 110, hereinafter referred as a memory 110 and a data repository 112, for example, a repository 112. The memory 110 is in communication with the one or more hardware processors 108, wherein the one or more hardware processors 108 are configured to execute programmed instructions stored in the memory 110, to perform various functions as explained in the later part of the disclosure. The repository 112 may store data processed, received, and generated by the system 100.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

According to an embodiment of the disclosure, the computing device 102 is communication with a plurality of motion sensors 114. The plurality of motion sensors 114 is configured to sense the movement of the person at a predefined time interval over a time period. The data collected from the plurality of motion sensors 114 is referred as an input data or a first set of input data. The plurality of motion sensors 114 is present in a plurality of rooms at a facility, wherein the plurality of rooms comprises one or more living rooms, one or more bedrooms, one or more kitchen and one or more bathrooms. In the elderly home monitoring system, the plurality of motion sensors 114 comprises passive infrared (PIR) motion sensors and magnetic door contact sensors to the elderlies' homes. These sensors are non-image capturing and non-audio detection and are basically non-invasive in nature and privacy preserving.

Figure 2:
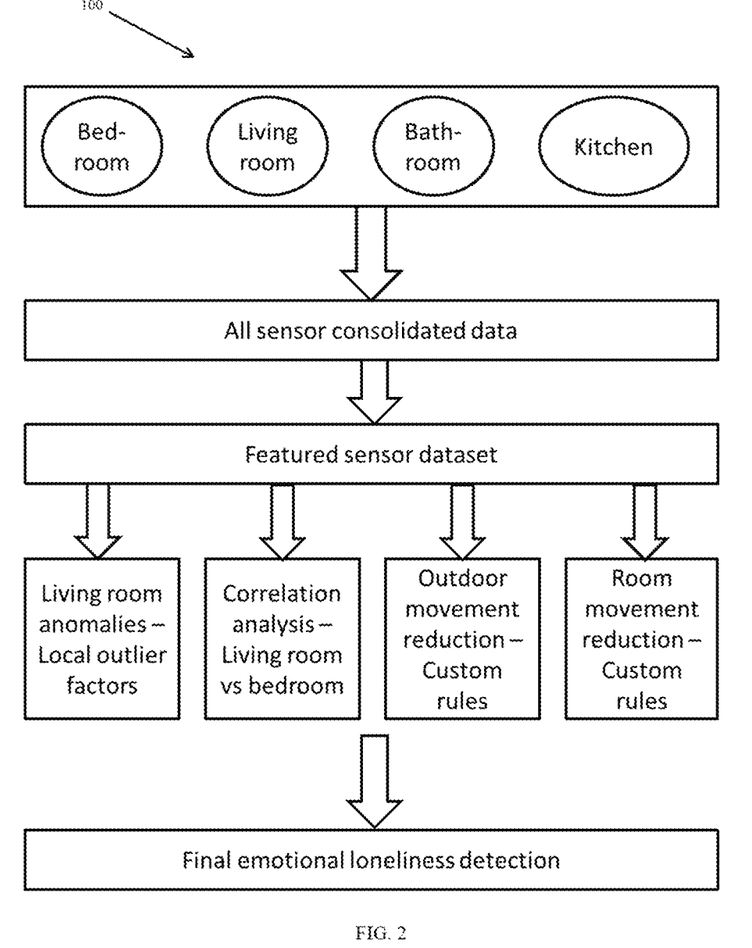
FIG. 2 is a schematic representation of the non-obtrusive method for detection of emotional loneliness of the person according to some embodiments of the present disclosure.

In the present disclosure, the time period looked at was daytime from 7 AM to 7 PM, and the night-time from 7:01 PM to 6:59 AM for a predefined time duration. The system 100 is using a 4-step approach to tease out the emotional loneliness activity as shown in the schematic architecture of FIG. 2. As shown in the figure, the first step is the consolidation of raw sensor data from the plurality of motion sensors 114. The second step is creation of featured sensor data set. The third step is emotional isolation algorithm step. In this step, the emotional state of the person is determined using four methodology, i.e. (i) anomalies detected in the living room using a local outlier factor model. (ii) Correlation analysis between bedroom and living room, (iii) outdoor activity analysis and (iv) room change analysis. These methodologies have been explained in the later part of the disclosure. Finally, the fourth step is final emotional loneliness determination using above four methodologies.

Figure 3:
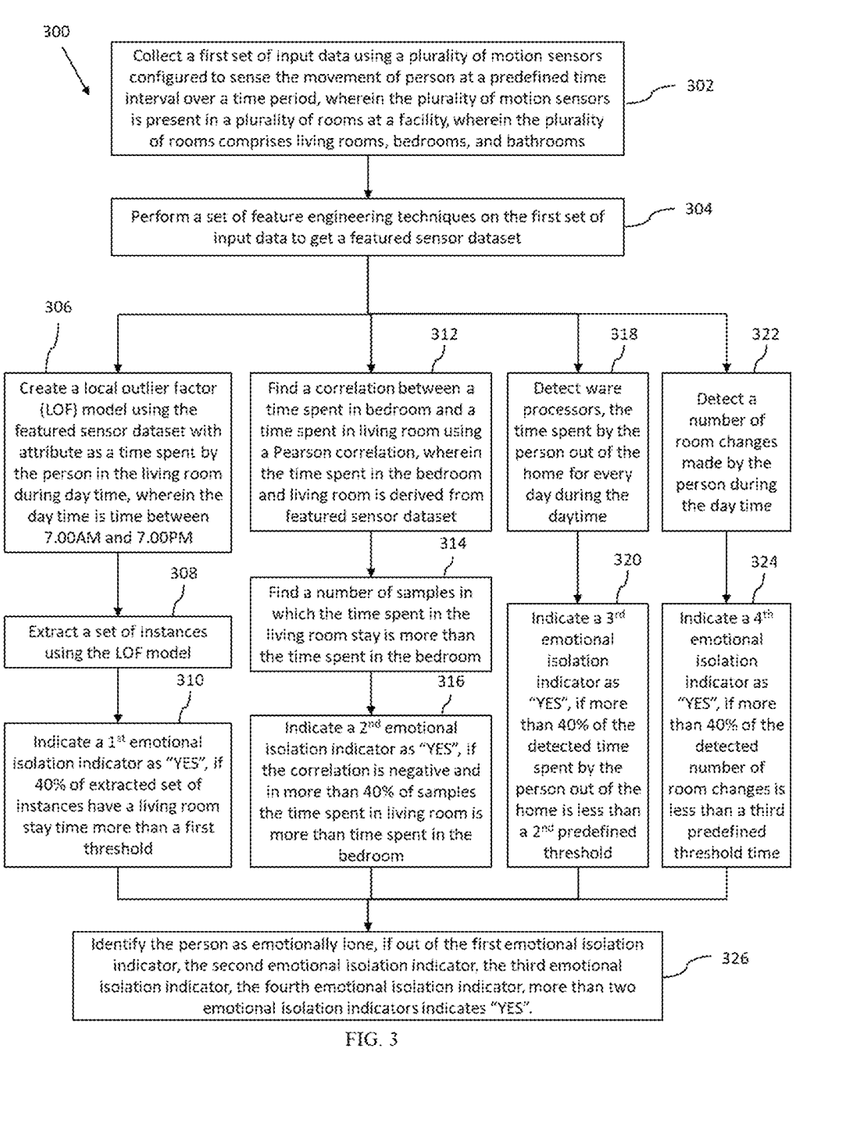
FIG. 3 is a flowchart illustrating the non-obtrusive method for detection of emotional loneliness of the person according to some embodiments of the disclosure.

FIG. 3 illustrates an example flow chart of a method 300 for non-obtrusive detection of emotional loneliness of the person, in accordance with an example embodiment of the present disclosure. The method 300 depicted in the flow chart may be executed by a system, for example, the system 100 of FIG. 1. In an example embodiment, the system 100 may be embodied in the computing device.

Operations of the flowchart, and combinations of operations in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 100. However, the operations of the method 300 can be described and/or practiced by using any other system.

Initially at step 302 of the method 300, a first set of input data is collected using the plurality of motion sensors 114. The plurality of motion sensors 114 are passive infrared sensors and door sensors and are configured to sense the movement of the person at a predefined time interval over a time. The plurality of motion sensors 114 is present in a plurality of rooms at a facility such as the home, wherein the plurality of rooms comprises one or more living rooms, one or more bedrooms, a kitchen and one or more bathrooms.

The plurality of motion sensors 114 is present/deployed in various parts of the homes and emanates data at regular intervals. In an example, the interval is a 10-second interval. The data from these sensors are then aggregated into one single view—a sample view sensor data is provided in TABLE 1. Here, each row of the data provides a resident ID, a sensor ID, location of the sensor (i.e. which specific room in that instance) and a timestamp at which the reading is captured. From this set of data, it can be seen that the elderly resident has moved across the various rooms.

TABLE 1

Sample aggregated data view

| Resident ID | Sensor ID | Location | Time stamp |
|---|---|---|---|
| Resident 1 | 482-m-01 | Living room | 2017 Nov. 1 T00:01:34 |
| Resident 1 | 483-m-01 | Bedroom | 2017 Nov. 1 T00:01:42 |
| Resident 1 | 483-m-01 | Bathroom | 2017 Nov. 1 T00:18:51 |
| Resident 1 | 480-m-01 | Kitchen | 2017 Nov. 1 T00:18:52 |

Further at step 304 of the method 300, a set of feature engineering techniques is performed on the first set of input data to get a featured sensor dataset. The featured sensor dataset comprises meaningful information of the input data. The raw sensor data is mined into useful "features" to form the "featured sensor dataset". By creating as many features as possible, enables the dataset to become more detailed and clear. This helps in establishing nocturia patterns. As illustration, an example of the sample featured dataset is represented in TABLE 2.

TABLE 2

Sample featured sensor dataset

| Time stamp | Resident ID | Day time | From location | To location | Room change indicator | Time spent | Time period |
|---|---|---|---|---|---|---|---|
| May 1, 2019 1:05 | Resident 1 | N | Living room | Bedroom | Y | 3 | E9 to 6 |
| May 1, 2019 1:23 | Resident 1 | N | Bedroom | Bedroom | N | 5 | E9 to 6 |
| May 1, 2019 1:23 | Resident 1 | N | Bedroom | Bedroom | N | 1091 | E9 to 6 |
| May 1, 2019 1:24 | Resident 1 | N | Bedroom | Bathroom | Y | 8 | E9 to 6 |
| May 1, 2019 1:28 | Resident 1 | N | Bathroom | Bathroom | N | 5 | E9 to 6 |

From a comparison of Table 2 with Table 1, it can be deduced that more detailed information is available in Table 2, which includes "Daytime", "From Location", "To Location", "Time Spent" (in a specific location), "Time Period" (whether it is morning, evening, afternoon, etc.) and "Room Change Indicator" (i.e. if the elderly resident has moved between different rooms). It should be appreciated that various other parameters can also be derived using the featured sensor dataset based on the requirement. To understand the data further, the "Room Change Ind" becoming "Y" if the "From Location" and the "To Location" are different—this implied that the resident has moved between living room to bedroom (in the first instance); and when the "Room Change Indicator" becomes "N", this means the resident is staying in the same room. Such level of clarity arising from the featured dataset reveal the emotional loneliness patterns in a simplistic way, thereby opening up the options to mine the dataset further.

Further step 306 to step 310 of the method 300 provides details detection of emotional isolation using a local outlier factor (LOF) model to detect anomalies in the living room. At step 306, the local outlier factor (LOF) model is created using the featured sensor dataset with attribute as a time spent by the person in the living room during day time, wherein in an example the day time is time between 7.00 AM and 7.00 PM. The user can change the time as per the requirement. At step 308, a set of instances is extracted using the LOF model. And at step 310, a first emotional isolation indicator is indicated as "YES", if 40% of extracted set of instances have a living room stay time more than a first threshold. The first threshold is addition of a mean of the time spent in the living room and a standard deviation of the time spent in the living room.

Figure 4:
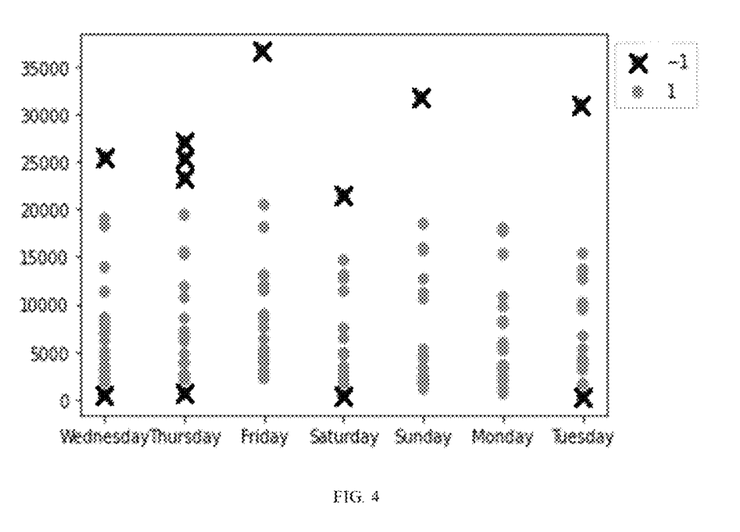
FIG. 4 illustrates graphical representation of data points derived using the LOF model from a sample input data accordance with some embodiments of the present disclosure.

A graphical representation of the data points derived using the LOF model for a sample input data is shown in FIG. 4. For the sample input data, FIG. 4 visualizes normal and anomaly points. Instances labeled as "−1" are identified as outliers.

Further step 312 to 316 of the method 300 provides details of the detection of emotional isolation using correlation analysis between the bedroom and the living room. At step 312, a correlation is found between a time spent in the bedroom and a time spent in the living room using a Pearson correlation. The time spent in the bedroom and living room is derived from the featured sensor dataset. At step 314, a number of samples is found in which the time spent in the living room stay is more than the time spent in the bedroom. And at step 316, a second emotional isolation indicator is indicated as "YES", if the correlation is negative and in more than 40% of samples the time spent in living room is more than time spent in the bedroom.

Figure 5:
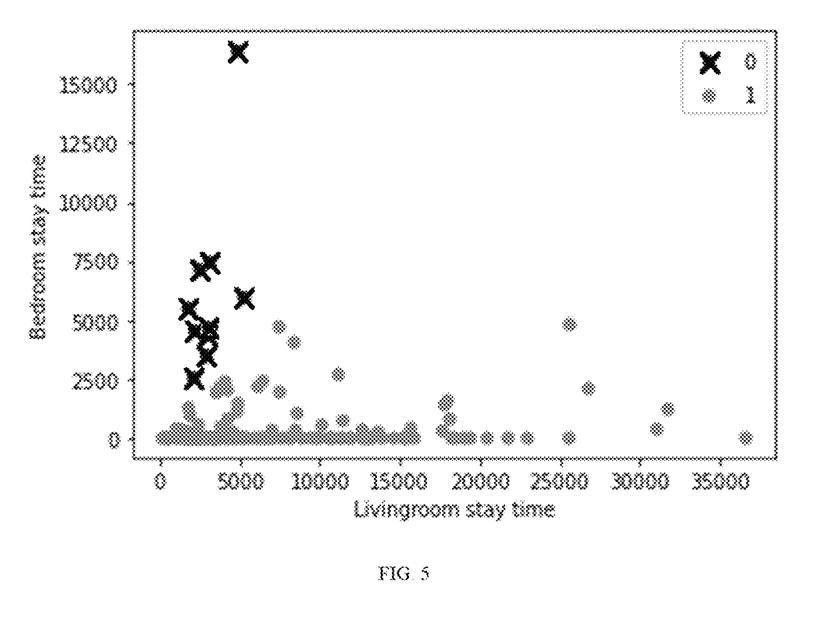
FIG. 5 illustrates graphical representation of the data instances derived from the correlation analysis using the sample input data according to some embodiments of the present disclosure.

A graphical representation of the data instances derived from the correlation analysis for the sample input data is shown in FIG. 5. The plot in FIG. 5 shows, instances which labeled as one have greater living room stay time where more than 50% of the data in this case satisfies above condition and they are negatively correlated. So by correlation analysis using correlation function and by querying for actual living room data vs bedroom stay, it can be deduced that the resident is emotionally isolated.

Further step 318 to 320 of the method 300 provides details of the detection of emotional isolation using outdoor activity analysis. At step 318, the time spent by the person out of the home is detected for every day during the daytime. And at step 320, a third emotional isolation indicator is indicated as "YES", if more than 40% of the detected time spent by the person out of the home is less than a second predefined threshold. The second threshold is addition of a mean of the time spent in the outdoor and a standard deviation of time spent in the outdoor.

Figure 6:
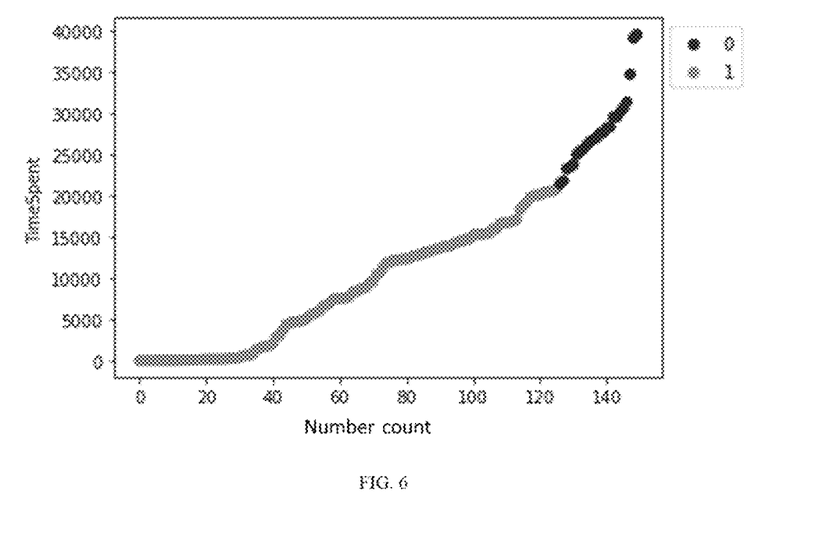
FIG. 6 illustrates a graphical illustration of data points identified using outdoor activity analysis for the sample input data according to some embodiments of the present disclosure.

A graphical illustration of data points identified using outdoor activity analysis for the sample input data is shown in FIG. 6. For the resident, the plot in FIG. 6 identifies points which are below the second threshold (1) and points above the second threshold. From the plot we can see that more than 40% points lies below the second threshold.

Further step 322 to 324 of the method 300 provides details of the detection of emotional isolation using a room change analysis. At step 322, a number of room changes made by the person during the day time are detected. And at step 324, a fourth emotional isolation indicator as "YES", if more than 40% of the detected number of room changes is less than a third threshold time. The third threshold time is addition of a mean of the number of room changes made by the person during day time and the standard deviation of the room changes made by the person during day time.

Figure 7:
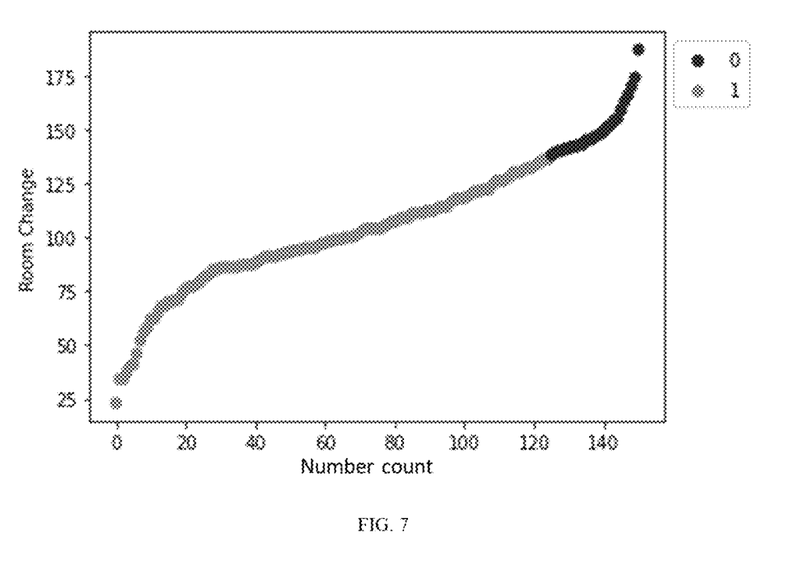
FIG. 7 illustrates a graphical illustration of data points identified using room change analysis for the sample input data according to some embodiments of the present disclosure.

A graphical illustration of data points identified using room change analysis for the sample input data is shown in FIG. 7. For the resident, the plot in FIG. 7 identifies points which are below the third threshold (1) and points above the third threshold. From the plot it can be deduced that more than 40% points lies below the third threshold.

And finally at step 326 of the method 300, the person is identified as emotionally lone, if out of the first emotional isolation indicator, the second emotional isolation indicator, the third emotional isolation indicator, the fourth emotional isolation indicator, more than two emotional isolation indicators indicate "YES".

According to an embodiment of the disclosure, the system 100 is also configured to identify Saturday and Sunday as weekends for detecting emotional loneliness with respect to weekends. There are chances when the emotional loneliness of the individual may increase or decrease.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of detecting emotional isolation of the person without disturbing person's privacy. The embodiment, thus provides a non-obtrusive method and system for detection and validation of emotional isolation for the person. Further, the embodiments are also configured to provide accurate indication of the emotional isolation as compared to the prior art.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

We claim:

1. A processor implemented method for detection of emotional loneliness of a person, the method comprising:
   collecting a first set of input data using a plurality of motion sensors configured to sense movement of the person at predefined time intervals over a time period, wherein the plurality of motion sensors is present in a plurality of rooms at a facility, wherein the plurality of rooms comprises one or more living rooms, one or more bedrooms, and one or more bathrooms;
   performing, via one or more hardware processors, a set of feature engineering techniques on the first set of input data to get a featured sensor dataset;
   creating, via the one or more hardware processors, a local outlier factor (LOF) model using the featured sensor dataset with time spent by the person in the living room during day time as an attribute, wherein the day time is time between 7.00 AM and 7.00 PM;
   extracting, via the one or more hardware processors, a set of instances using the LOF model;

indicating, via the one or more hardware processors, a first emotional isolation indicator as "YES", if 40% of extracted set of instances have a time spent in the living room is more than a first threshold;

finding, via the one or more hardware processors, a correlation between a time spent in the bedroom and a time spent in the living room using a Pearson correlation, wherein the time spent in the bedroom and living room is derived from featured sensor dataset;

finding, via the one or more hardware processors, a number of samples in which the time spent in the living room stay is more than the time spent in the bedroom;

indicating, via the one or more hardware processors, a second emotional isolation indicator as "YES", if the correlation is negative and in more than 40% of samples the time spent in living room is more than time spent in the bedroom;

detecting, via the one or more hardware processors, the time spent by the person outside the facility for every day during the daytime;

indicating, via the one or more hardware processors, a third emotional isolation indicator as "YES", if more than 40% of the detected time spent by the person out of the home is less than a second predefined threshold;

detecting, via the one or more hardware processors, a number of room changes made by the person during the day time;

indicating, via the one or more hardware processors, a fourth emotional isolation indicator as "YES", if more than 40% of the detected number of room changes is less than a third threshold time; and identifying, via one or more hardware processors, the person being as emotionally lone, if out of the first emotional isolation indicator, the second emotional isolation indicator, the third emotional isolation indicator, and the fourth emotional isolation indicator, more than two emotional isolation indicators indicates "YES".

2. The method of claim 1, wherein the first set of input data comprises a unique ID of the person, sensor ID corresponding to each of the plurality of motion sensors, a sensor location and a timestamp.

3. The method of claim 1, wherein the first threshold is addition of a mean of the time spent in the living room and a standard deviation of the time spent in the living room.

4. The method of claim 1, wherein the second threshold is addition of a mean of the time spent in the outdoor and a standard deviation of time spent in the outdoor.

5. The method of claim 1, wherein the third threshold is addition of a mean of the number of room changes made by the person during the day time and the standard deviation of the room changes made by the person during day time.

6. The method of claim 1, wherein the plurality of motion sensors comprises passive infra-red (PIR) motion sensors and magnetic door contact sensors.

7. The method of claim 1 further comprising identifying Saturday and Sunday of every week as weekends for detecting emotional loneliness with respect to weekends.

8. A system for detection of emotional loneliness of a person, the system comprises:

a plurality of motion sensors for collecting a first set of input data, the plurality of motion sensors configured to sense movement of the person at predefined time intervals over a time period, wherein the plurality of motion sensors is present in a plurality of rooms at a facility, wherein the plurality of rooms comprises one or more living rooms, one or more bedrooms, and one or more bathrooms;

one or more hardware processors; and a memory in communication with the one or more hardware processors, wherein the one or more hardware processors are configured to execute programmed instructions stored in the memory, to:

perform a set of feature engineering techniques on the first set of input data to get a featured sensor dataset;

create a local outlier factor (LOF) model using the featured sensor dataset with time spent by the person in the living room during day time as an attribute, wherein the day time is time between 7.00 AM and 7.00 PM;

extract a set of instances using the LOF model;

indicate a first emotional isolation indicator as "YES", if 40% of extracted set of instances have a time spent in the living room is more than a first threshold;

find a correlation between a time spent in the bedroom and a time spent in the living room using a Pearson correlation, wherein the time spent in the bedroom and living room is derived from featured sensor dataset;

find a number of samples in which the time spent in the living room stay is more than the time spent in the bedroom;

indicate a second emotional isolation indicator as "YES", if the correlation is negative and in more than 40% of samples the time spent in living room is more than time spent in the bedroom;

detect the time spent by the person outside the facility for every day during the daytime;

indicate a third emotional isolation indicator as "YES", if more than 40% of the detected time spent by the person out of the home is less than a second predefined threshold;

detect a number of room changes made by the person during the day time;

indicate a fourth emotional isolation indicator as "YES", if more than 40% of the detected number of room changes is less than a third predefined threshold time; and identify the person being as emotionally lone, if out of the first emotional isolation indicator, the second emotional isolation indicator, the third emotional isolation indicator, and the fourth emotional isolation indicator, more than two emotional isolation indicators indicate "YES".

9. The system of claim 8, wherein the first set of input data comprises a unique ID of the person, sensor ID corresponding to each of the plurality of motion sensors, a sensor location and a timestamp.

10. The system of claim 8, wherein the first threshold is addition of a mean of the time spent in the living room and a standard deviation of the time spent in the living room.

11. The system of claim 8, wherein the second threshold is addition of a mean of the time spent in the outdoor and a standard deviation of time spent in the outdoor.

12. The system of claim 8, wherein the third threshold is addition of a mean of the number of room changes made by the person during the day time and the standard deviation of the room changes made by the person during day time.

13. The system of claim 8, wherein the plurality of motion sensors comprises passive infra-red (PIR) motion sensors and magnetic door contact sensors.

14. The system of claim 8 further configured to identify Saturday and Sunday of every week as weekends for detecting emotional loneliness with respect to weekends.

15. One or more non-transitory machine readable information storage mediums comprising one or more instructions which when executed by one or more hardware processors cause managing a plurality of events, the instructions cause:

- collecting a first set of input data using a plurality of motion sensors configured to sense movement of the person at predefined time intervals over a time period, wherein the plurality of motion sensors is present in a plurality of rooms at a facility, wherein the plurality of rooms comprises one or more living rooms, one or more bedrooms, and one or more bathrooms;
- performing a set of feature engineering techniques on the first set of input data to get a featured sensor dataset;
- creating a local outlier factor (LOF) model using the featured sensor dataset with time spent by the person in the living room during day time as an attribute, wherein the day time is time between 7.00 AM and 7.00 PM;
- extracting a set of instances using the LOF model;
- indicating a first emotional isolation indicator as "YES", if 40% of extracted set of instances have a time spent in the living room is more than a first threshold;
- finding a correlation between a time spent in the bedroom and a time spent in the living room using a Pearson correlation, wherein the time spent in the bedroom and living room is derived from featured sensor dataset;
- finding a number of samples in which the time spent in the living room stay is more than the time spent in the bedroom;
- indicating a second emotional isolation indicator as "YES", if the correlation is negative and in more than 40% of samples the time spent in living room is more than time spent in the bedroom;
- detecting the time spent by the person outside the facility for every day during the daytime;
- indicating a third emotional isolation indicator as "YES", if more than 40% of the detected time spent by the person out of the home is less than a second predefined threshold;
- detecting a number of room changes made by the person during the day time;
- indicating a fourth emotional isolation indicator as "YES", if more than 40% of the detected number of room changes is less than a third threshold time; and
- identifying the person being as emotionally lone, if out of the first emotional isolation indicator, the second emotional isolation indicator, the third emotional isolation indicator, and the fourth emotional isolation indicator, more than two emotional isolation indicators indicates "YES".

* * * * *